United States Patent [19]

Uchigaki et al.

[11] Patent Number: 4,585,007

[45] Date of Patent: Apr. 29, 1986

[54] METHOD FOR CONTINUOUSLY MEASURING A SPECIFIED INGREDIENT IN A DILUTED LIQUID

[75] Inventors: Takatoshi Uchigaki; Hiroshi Hyodo; Teijiro Iwase, all of Kyoto, Japan

[73] Assignee: Kabushiki Kaisha Kyoto Daiichi Kagaku, Japan

[21] Appl. No.: 493,415

[22] Filed: May 10, 1983

[30] Foreign Application Priority Data

May 15, 1982 [JP]  Japan .................................. 57-82009

[51] Int. Cl.$^4$ ............................................. A61B 5/00
[52] U.S. Cl. ................................................... 128/632
[58] Field of Search ......................................... 128/632

[56] References Cited

U.S. PATENT DOCUMENTS

| | | | |
|---|---|---|---|
| 3,518,982 | 7/1970 | Timmins et al. | 128/632 |
| 3,983,864 | 10/1976 | Sielaff et al. | 128/632 |
| 4,016,864 | 4/1977 | Sielaff et al. | 128/632 |
| 4,340,615 | 7/1982 | Goodwin et al. | 128/632 X |
| 4,401,122 | 8/1983 | Clark | 128/632 X |
| 4,403,984 | 9/1983 | Ash et al. | 128/632 X |
| 4,444,193 | 4/1984 | Foyt et al. | 128/632 |

Primary Examiner—Edward M. Coven
Attorney, Agent, or Firm—Darby & Darby

[57] ABSTRACT

A method for accurately performing concentration measurements while compensating the dilution ratio as needed during continuous measurement of specified ingredient in the liquid to be tested. The liquid to be tested is diluted by a diluent, wherein the liquid to be tested and the diluent or the mixture of the two and the diluent is transferred by means of the respective tube pumps to a measuring section. Either or both of the quantities of liquid-feeding of those two liquids are changed at the beginning of measuring or in an optional stage during the time of the measurement, diluted and mixed at two or more dilution ratios. Then the real dilution ratio at the time of changing the quantities of the said liquids is found on the basis of the measured value of the substance to be measured at the respective dilution ratios, and the concentration of the substance contained in the liquid to be tested is determined by using the real dilution ratio.

4 Claims, 6 Drawing Figures

4,585,007

METHOD FOR CONTINUOUSLY MEASURING A SPECIFIED INGREDIENT IN A DILUTED LIQUID

BACKGROUND OF THE INVENTION

This invention relates generally to a method and also an apparatus for continuously measuring a specified ingredient contained in a liquid to be tested, and, more particularly, to a method and apparatus wherein accurate measurement of concentration may be performed by compensating the dilution ratio as necessary during continuous measurement of the liquid under test as diluted by a diluent while using a tube pump for feeding the liquid.

It is common, when measuring the concentration of a specified ingredient (the substance to be measured) contained in a liquid to be tested, to supply to the measuring device a mixture of the liquid under test and some other liquid (in other words, the liquid to be tested is diluted th other liquid) and not necessarily a single liquid. There are many purposes for such dilution for example, for pH adjustment, the removal of interfering matter, the prevention of coagulation in a blood sample, and others. All these treatments, however, are liable to cause errors in the measured values of concentration due to errors in or scattering of the mixing rate (dilution ratio). In particular, when continuously selecting the liquid under test which is flowing through a particular channel and whose concentration is continuously monitored, it is often difficult to keep the dilution ratio constant, and the fluctuation is directly expressed in errors of the measured value.

For example, in an apparatus wherein blood is drawn from a vein of a patient by the use of a double current catheter while infusing an anticoagulant in order to continuously and automatically monitor the concentration of a specified ingredient (for example, glucose) contained in the blood, a device for feeding liquid to the blood drawing part of the catheter is generally employed. Such device may be a tube pump having few pulsations and little dead volume that is able to continuously feed a very small quantity of liquid. The discharge quantity of such pumps, however, changes over time and causes the dilution ratio to fluctuate when used for continuous measurement for many hours. Therefore, it is difficult to accurately measure the correct value. This is attributable to deterioration or deformation over time of the pump's tubes because they are continuously squeezed. Also, the inner diameter of the tubes changes due to the adhesion of the constituents of the liquids to the inner tube walls.

In order to avoid these problems and compensate for the change in dilution ratio, heretofore a method has been adopted in which a double current catheter is detached from the patient in the middle of a measurement, and made to draw in a reference liquid. After the dilution ratio is compensated, the catheter is reattached to the patient. When using this method, however, the measurement is not only interrupted but also becomes inconvenient. Further, the patient is susceptible to infection since the catheter must be withdrawn and reinserted.

In order to eliminate these problems, there is disclosed in the Japanese patent application disclosure No. 135795 of 1977, a technique in which the dilution ratio is compensated by comparing the blood separately drawn from a vein of the patient by the use of a syringe with the blood sample drawn from the catheter. However, drawing blood separately by syringe not only causes pain to the patient but also increases the quantity of blood loss. Also, it is required for the blood sample drawn by syringe to be treated with an anticoagulant within a prescribed short time, and to be diluted accurately to a prescribed value. This is a very complex procedure.

As mentioned above, the conventional method of compensating the dilution ratio while continuously drawing blood causes pain and danger of infection to the patient, requires many people and is very complicated, involving the possibility of errors attributable to mistakes in the procedure.

SUMMARY OF THE INVENTION

It is an object of this invention to eliminate the problems discussed and to provide a method by which the measurement of concentration can be performed stabley and accurately for many hours during continuous measurement of a liquid to be tested that is diluted by a diluent. In addition, th invention provides a method by which accurate measurement of concentration can be performed by continuously diluting the liquid to be tested using a tube pump and a double current catheter.

Another object of this invention is to provide a method and apparatus by and in which the compensating motion can be automated, the compensation of the dilution ratio can be done automatically at periods prescribed in advance, and a measurement of high accuracy can be performed continuously.

Further, it is an object to provide a method in which the compensation of the dilution ratio by the reference liquid conducted before the commencement of the measurement is dispensed with.

Yet another object is to permit compensation of the dilution ratio to be made by using a reference liquid whose concentration is unknown.

A further object of this invention is to provide an apparatus which has the ability to compensate (recheck) the dilution ratio while it is still connected to the double current catheter which is inserted into the human body (patient) and without the necessity of any manual operation.

These objects can be achieved by finding a real dilution ratio while changing the quantities of liquid fed from either or both of two tube pumps in which each transfers either a liquid to be tested and a diluent or the mixture of the above two and a diluent.

Other objects of the invention will become apparent from the following detailed description and the annexed drawings.

DETAILED DESCRIPTION

Considering the case of continuous measurement of the blood sugar value (glucose concentration) in the blood sample using a double current catheter, a detailed description is directed to the method and apparatus of the invention with reference to the accompanying drawings.

Figure 1:
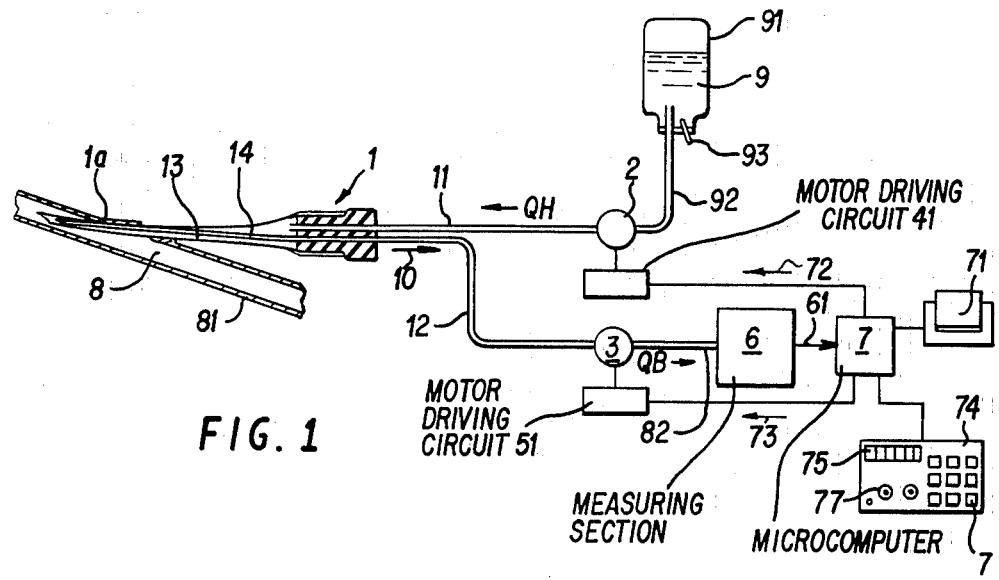
FIG. 1 is a schematic drawing showing an example of the invention.
Figure 2:
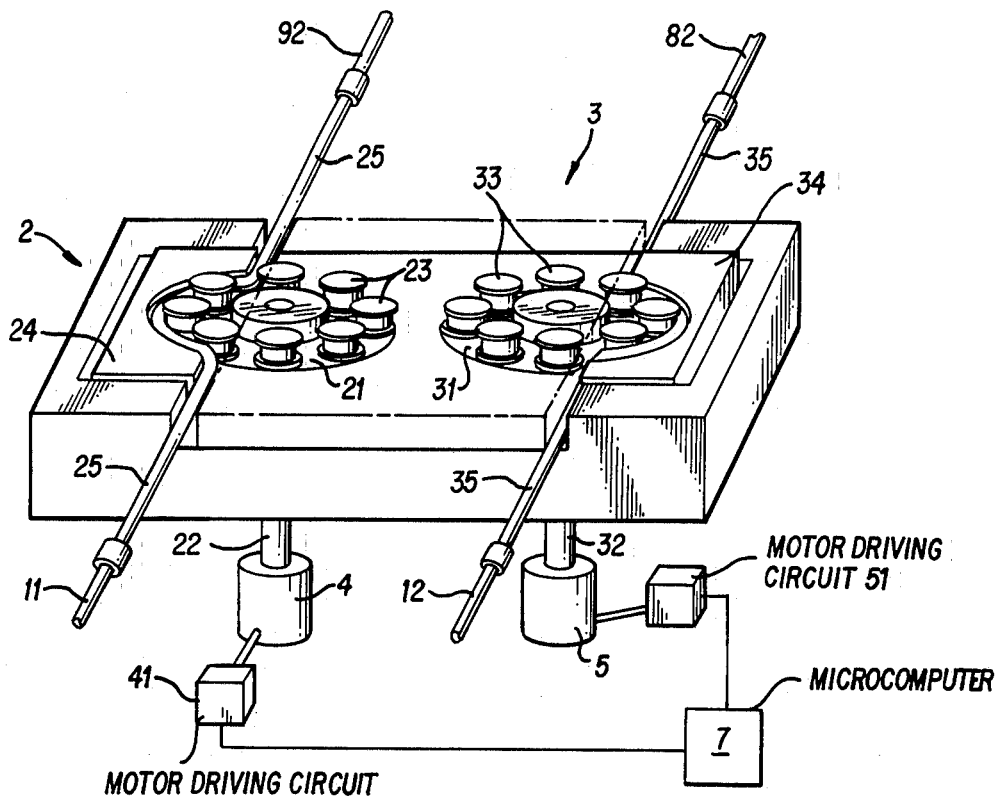
FIG. 2 is a perspective view of a part of a tube pump.

FIG. 1 is a schematic drawing showing an example of the apparatus according to the present invention, and FIG. 2 is a persepctive view of a part of a tube pump thereof. In the figures, reference numeral (1) indicates a double current catheter, numerals (11) and (12) are catheter tubes, numerals (2) and (3) are tube pumps, and numerals (4) and (5) are pulse motors which force tube pumps (2) and (3) to be rotationally driven. Numeral (6) indicates the measuring section, while numeral (7) is a microcomputer, and numeral (71) is an indicating device. Reference numerals (41) and (51) indicate pulse motor driving circuits for the first and second rotationally driving devices, and are conventional devices that generate a signal to drive motors 2 and 3. Arrows (72) and (73) are control signals (speed change command signals) which are generated by microcomputer (7). In accordance with these signals (72) and (73), the number of revolutions of the tube pumps (2) and (3) can be optionally changed. Further, reference numerals (21) and (31) indicate rotors of the tube pumps (2) and (3), respectively, numerals (22) and (32) indicate rotor shafts, numerals (23) and (33) indicate rollers, numerals (24) and (34) indicate pump heads, and numerals (25) and (35) are pump tubes.

Double current catheter (1) is inserted into the inside of a canula (1a) whose tip is to be inserted into a vein in a patient. The gap between both (1) and (1a) forms an anticoagulant reservoir (13). Anticoagulant (9) is sent through an anti-coagulant feeding tube (92) and a first catheter tube (11) into anticoagulant reservoir (13) by the feeding action of tube pump (2). In this connection, reference numeral (93) in FIG. 1 indicates an air introducing needle.

On the other hand, the blood sample (liquid to be tested) (8) is drawn in, at the tip part of a sucking tube (14) of the catheter by the sucking action of a second tube pump (3) while being mixed with (or diluted by) the anticoagulant (9), to form a mixed liquid (10). Mixed liquid (10) passes through the sucking tube (14) of the catheter, the second catheter tube (12), and a mixed liquid-feeding tube (82), and reaches the measuring section (6). In measuring section (6), a measuring signal (61) corresponding to the glucose concentration in the mixed liquid (10) is generated from, for example, an immobilized enzyme film electrode. Measuring signal (61) is input into an arithmetic memory system of microcomputer (7) or the like, from which the blood-sugar value is calculated on the basis of an operation described later. This value is displayed on the indicating device (71).

In this case, the dilution ratio δ is the ratio by volume of the mixed liquid (10) to the blood sample (8). Supposing the quantity of discharge of the tube pump (2) is QH and that of the tube pump (3) is QB, the following equation is obtained:

$$\delta = QB/(QB-QH)$$

Further, the dilution ratio δ also is equal to the ratio of the blood sugar value X in the blood sample (8) and also to the glucose concentration G in the mixed liquid (10), therefore:

$$\delta = X/G \qquad (1)$$

(In the following, the blood sugar value X means the glucose concentration in the blood sample and is distinguished from the glucose concentration G in the mixed liquid.)

From the above two equations, the blood-sugar value X may be found by the following equation:

$$X = \delta \cdot G = QB \cdot G/(QB-QH) \qquad (2)$$

Conventionally, when a measuring signal (61) corresponding to G is obtained, the value of δ is regarded as a the correct one obtained ahead of time and is displayed on the indicating device as X. Possible fluctuation of the value of δ are not taken into consideration, and the fluctuating portion of the value of δ is expressed as an error. Aside from this, there has been adopted a method in which the compensation of the dilution ratio is made by using a reference liquid whose concentration is known or by using a blood sample drawn separately by the use of a syringe, as in the conventional technique discussed above, as a substitute for the continuously drawn blood sample.

In the present invention, δ, as given in equation 1 is successively stored in the microcomputer (7). There are many methods for storing these values, such as, for example, manually inputting them or having microcomputer (7) automatically store the values obtained by using the reference liquid whose concentration is known in place of the blood sample (8) or inputting the real value of the dilution ratio obtained in the process of the measurement described later.

After the dilution ratio $\delta_0$ obtained by using the reference liquid whose concentration is known is stored in the microcomputer prior to the measurement, the double-current catheter (1) is set in a vein of the patient in order to commence the measurement.

However, the above-mentioned QH and QB fluctuate over time for the reason discussed, in proportion to which the value of δ also varies. Even if such a variation were insignificant, its error cannot be ignored when the measurement continues over long hours.

The present invention permits finding real dilution ratios at any point in time, making the microcomputer (7) correctively store the above real dilution ratios in succession, and obtaining continuously accurate blood-sugar values (X) on the basis of the following principle:

First, assuming that the blood-sugar value of the blood sample (8) at a point in time $T_1$ is $X_1$, the glucose concentration in the mixed liquid (10) is $G_1$, the quantities of discharge of the tube pumps (2) and (3) are $QH_1$ and $QB_1$, respectively, and the real dilution ratio is $\delta_1$, the following equation 3 is found using equation 2:

$$X_1 = \delta_1 G_1 = QB_1 G_1/(QB_1 - QH) \qquad (3)$$

Then, if the number of revolutions of the first tube pump (2) is increased N times by changing control signal (72), the discharge quantity of the tube pump (2) also increases by N times because the number of revolutions of the pump and its output are proportionally related to each other. If the glucose concentration in the mixed liquid (10) under the above condition is $G_1'$, the blood-sugar value of the blood sample (8) is $X_1'$, the quantities of discharge of the tube pumps (2) and (3) are $QH_1'$ and $QB_1'$, respectively, and the real dilution ratio is $\delta_1'$, the following equation is obtained similarly using equation (2):

$$X_1' = {}_1'G_1' = QB_1'G_1'/(QB_1' - N \cdot QH_1') \qquad (4)$$

In this instance where the interval of the measurement is short, $X_1$ and $X_1'$ are substantially equivalent in view of the change over time of the blood-sugar value. Similarly the degree of deformation of the pump tubes (25) and (35) or the change of their inner diameter are negligible, so that $QB_1$ and $QB_1'$ as well as $QH_1$ and $QH_1'$ can be regarded as respectively equal. Therefore the real dilution ratio may be determined by eliminating the quantities of flow of the tube pumps from both equations (3) and (4). From these relations and equations (3) and (4) the following equation is obtained:

$$\delta_1 = X_1/G_1 = (NG_1 - G_1')/G_1(N-1) \tag{5}$$

The real dilution ratio $\delta_1$ can then be calculated on the basis of the above equation 5 which is stored in the microcomputer (7) in place of the dilution ratio $\delta_0$ mentioned previously. The blood-sugar value X which is thereafter calculated from dilution ratio $\delta_1$ equation (2) is displayed on measuring device (71).

It follows then that after a certain period of time $T_2$, $T_3$, the number of revolutions of the tube pump (2) is altered similarly to the above to obtain $\delta_2$, $\delta_3$, which are stored in succession. In this connection, the number of revolutions of the tube pump (2) at each period of time is temporarily increased N times and immediately thereafter restored to the original speed. Alternatively, after the measurement is completed, tube pump (2) is permitted to continue to operate at the increased number of revolutions during a first time $T_1$, but is increased by 1/N at the succeeding period of time $T_2$.

Therefore, even though the dilution ratio fluctuates due to the variations over time of the quantity of discharge of each of the tube pumps (2) and (3) at the time of the measurement, the dilution ratios made and stored in the microcomputer (7) are compensated successively to a value very near the real dilution ratio. It is thus possible to continuously make an accurate measurement of the blood-sugar value. There are many ways to store the dilution ratio in the microcomputer (7) for example, such as manually inputting numerical values read from the indicating window (75) of the operating section (74) using the input key (76), or storing them automatically by operating the dilution ratio-compensating switch (77).

In the above, a preferred embodiment of the present invention has been described with reference to the drawings. However, the invention is not limited thereto, but may be applied also to other various modifications as follows:

Although, in the above-described example, the number of revolutions of the tube pump (2) on the anticoagulant feeding side is increased by N times in order to find the respective glucose concentration values ($G_1$, $G_1'$) in the two kinds of mixed liquids, the number of rotations of tube pumps 2 and 3 may be increased by 1/N, if the tube pump (3) on the mixed liquid side is changed in speed or the both tube pumps (2) and (3) are changed in speed alternately or simultaneously. It is also desirable if this compensation (recheck) of the dilution ratio is made manually to the apparatus at any period of time, otherwise it may be set in the microcomputer (7) so as to be conducted automatically, for example, after 30 minutes, after 60 minutes, etc. Further the number of revolutions of either of the tube pumps (2) and (3) may be changed in several stages, for example, first by increasing it by N times at one period of time, or then by M times at a later period of time. In short, it does not matter even if the mixing rate (dilution ratio) is changed accordingly as the respective number of revolutions of either or both of the tube pumps are changed before and after a certain period of time. The respective values G can still be found.

Further, in the above-mentioned example, although the real dilution ratio was found by the first speed-change operation, the real dilution ratio may be determined by the average of the values of all dilution ratios obtained by repeating the speed-change operations as above several times at a certain period of time (in this case, it is permissible to apply the combination of various kinds of speed-change operations described above).

In the aforementioned example, the value of the blood sugar in the blood sample is arranged to be calculated by using the real dilution ratio obtained at the current period of time under the speed change operation of the tube pump until the next period of time. This calculation can also be made as follows:

In one instance the value of the blood-sugar is compensated by using the dilution ratio obtained under the speed change while tracing back partly before the speed-changing period of time (for example, up to the middle between the present speed-changing and last compensating periods of time). In another instance, while changing proportionally and distributively the two dilution ratios obtained at different periods of time, the value of the blood-sugar between both periods of time may be compensated successively by using the changing dilution ratios retroactively, and so on. In these cases, however, compensation is made after finding the blood sugar value, so that it is necessary to store the value not yet compensated. Such a modification is helpful particularly in the case where the dilution ratio fluctuates sharply.

Figures 3, 3A:
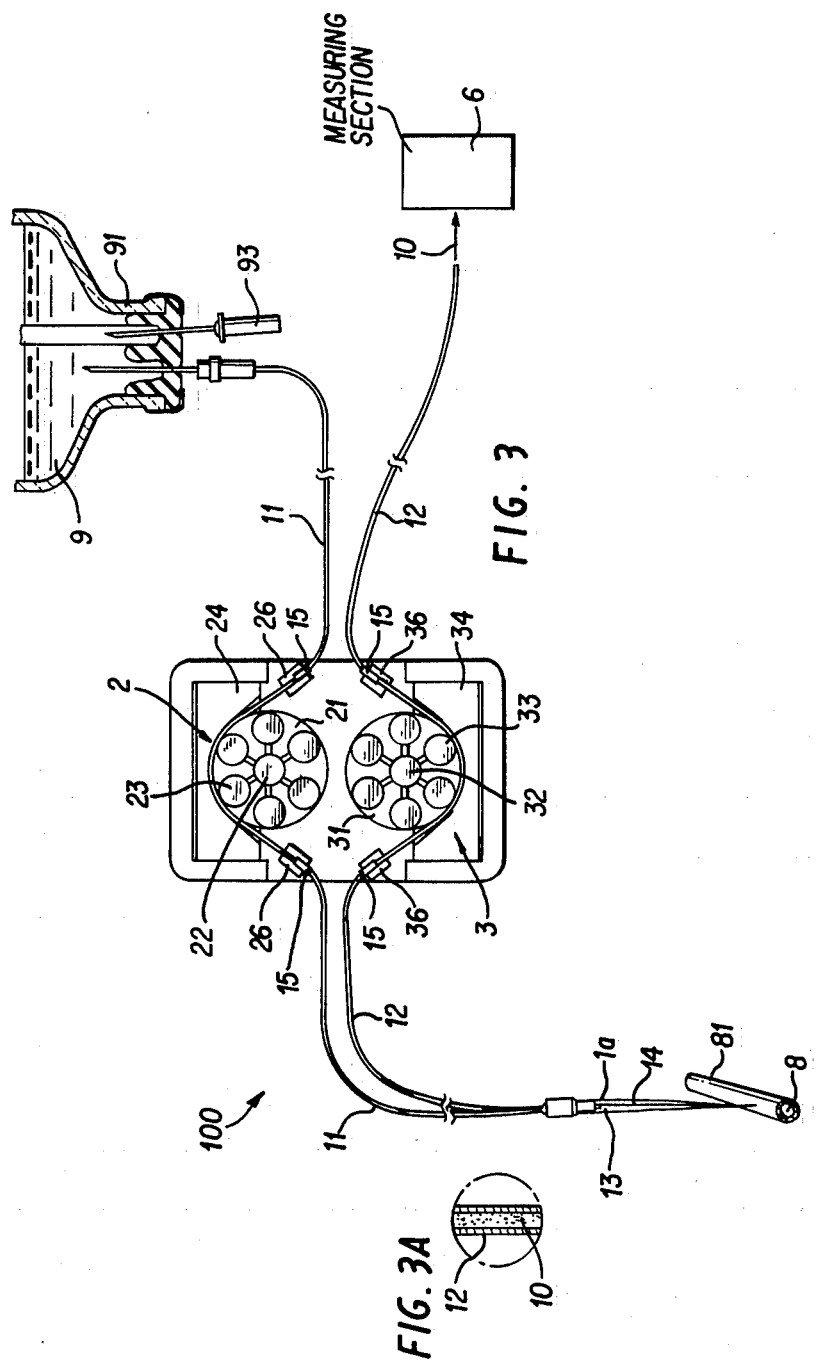
FIGS. 3 and 3(a) are a plan view showing a modification of the blood drawing section.

On the other hand, the driving source of the tube pumps (2) and (3) is not limited only to pulse motors, but may be any device capable of a variable speed of revolution, including those devices in which speed-change gearing is employed. Further, as an example of a modification of the blood drawing section, a double current catheter (100) can be used which is made so as to also perform the duties of both the pump tube (25) and anticoagulant feeding tube (92) and the tube (35) and mixed liquid feeding tube (82) in the former example, by making each of the catheter tubes (11) and (12) longer, as shown in FIG. 3. Reference numerals (15) in FIG. 3 indicate stoppers attached to the catheter tubes (11) and (12), and numerals (26) and (36) indicate stopper receivers provided in the tube pumps (2) and (3). This double current catheter (100) has various advantages including that it is subject to less sediment of foreign matter because both of its tubes (11) and (12) have no more than their end parts in their connecting points, it also has less danger of the tubes being clogged, the exchange of the catheter is made very easily and promptly, damage to the contact places with roller attributable to the speed change of the pumps (2) is eliminated, and (3) causes no problem from the tubes being exchangeable independently in each catheter, etc.

In all of the above-mentioned examples, the real dilution ratios varying progressively are rechecked while changing the number of revolutions of the tube pumps at a later period of time. The values thus obtained are stored in the microcomputer (7) in due succession, and a more accurate value of the blood sugar can be found. Comparing this obtained value of the real dilution ratio with the dilution ratio $\delta_o$ obtained by using the initial reference liquid at the beginning of measuring, a changing signal is fed back to, for example, the pulse motor driving circuits (41) and (51), whereby it is also possible to compensate the dilution ratio in such a manner as to return to the original dilution ratio. On the other hand, since the real blood sugar value $X_1$ at the above period of time can be found by the aforementioned equation (5), it does not matter if calculation is made only of the real blood sugar values, not the real dilution ratios, at regular intervals and to display them.

Figure 4A:
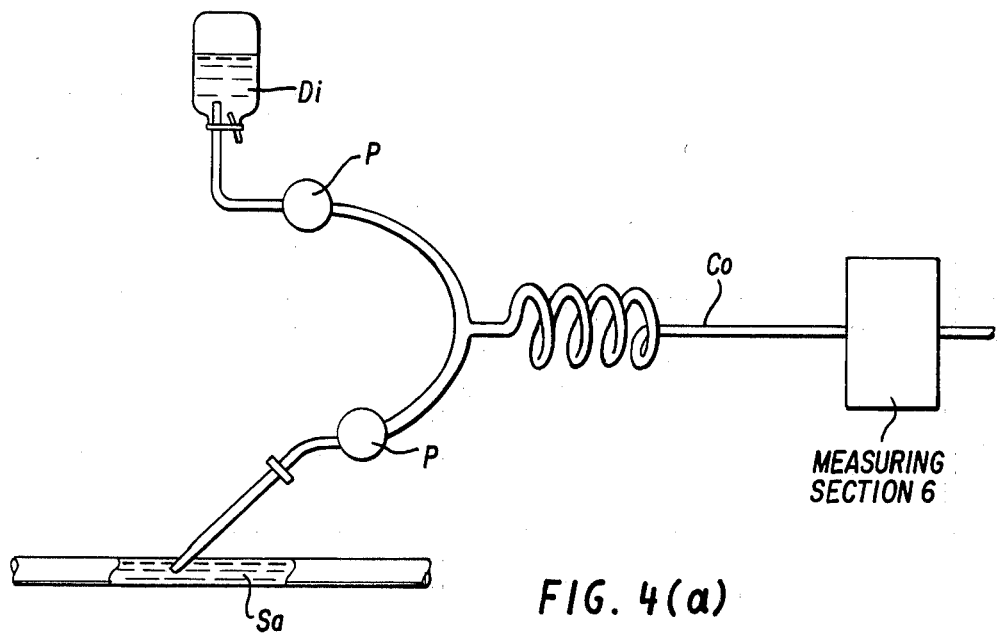
FIGS. 4(a) and (b) are schematic drawings showing other embodiments.
Figure 4B:
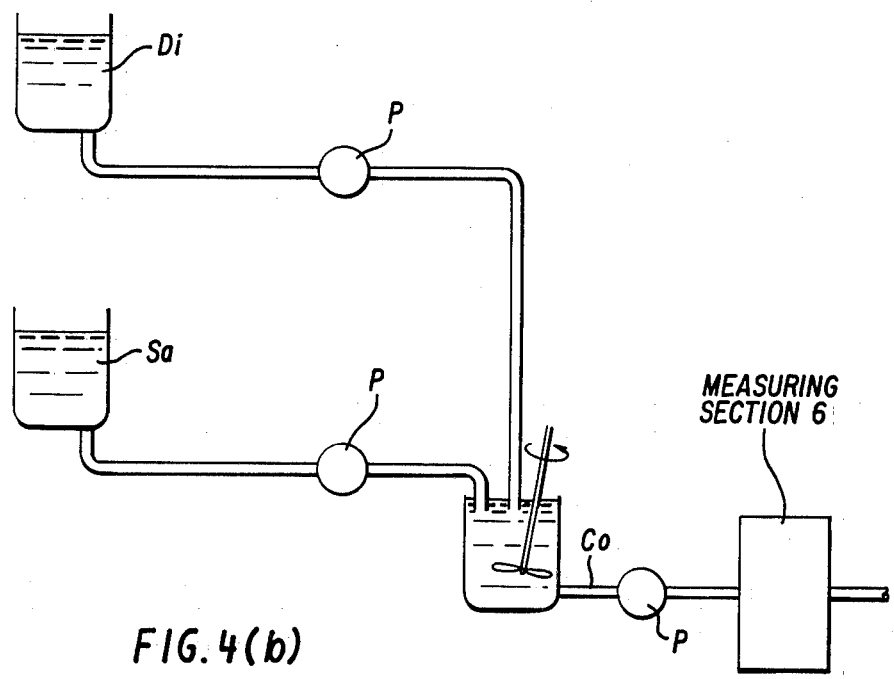

Further, the method and apparatus according to the present invention is properly used in the field of chemical analysis for continuously measuring specified ingredients, including the aforesaid analysis of blood. In addition, the method and apparatus is not limited to the case where the double current catheter is used in the manner as mentioned above; it may be also applied in the case where the progression of the mixed liquids ($C_o$) which are supplied to the measuring section (6) is observed with the passage of time: one mixed liquid has been obtained by transfering the liquid to be tested (Sa) and the diluent (Di) by the respective tube pumps (P) while mixing on the way, as shown in FIG. 4(a), and another mixed liquid by sending the liquid to be tested (Sa) and the diluent (Di) by the respective pumps (P) into the mixing vessel (C) while stirring.

As described above, the compensating method of the dilution ratio according to the present invention is one in which, in the case of finding the concentration of a specified substance contained in the liquid to be tested through the measurement of the concentration of the mixed liquid which is made by mixing the liquid to be tested with the diluent by the use of two tube pumps, the real dilution ratio and therefor the concentration is easily found with accuracy and certainly by controling the quantity of liquid fed to either or both of the tube pumps. Accordingly, even when such a measurement as the continuous meassuring of the blood sugar value is made for long hours, it becomes possible to perform the compensation (recheck) of the dilution ratio when the double current catheter is on the patient without its removal. As a result, there is no necessity of detaching the catheter during the middle of the measurement and of soaking it in the reference liquid.

The use of this catheter does not require separately drawing blood by a syringe for submitting to compensation. The method is safe and sanitary because maual intervention is not needed and does not increase pain to the patient. All things considered, the catheter according to the invention provides a technique of very high utility in the clinical medicine field. Further, this invention is able to automatize the compensating motion and to perform the automatic compensation of the dilution ratio at a preset period, so that it is possible for the analyser and the technician to make a measurement of high accuracy continuously, though being remote from the place where the measuring apparatus is set up. Thus, an economy of time and labor is brought about. Furthermore, in the apparatus of our invention it is also possible to eliminate various prior art disadvantages such as, for example, the deterioration and deformtion of the tube pumps over time, or the change in inner diameter of the tubes similarly over time, and consequently the present apparatus is well adapted to long periods of use, with the result that the total cost of the measuring operation is decreased.

Further, in this invention, it is not necessary that the reference liquid to be used for the compensation of the dilution ratio which will be performed prior to the commencement of the measurement have a known concentration. It suffices if only it is adjusted to approximately a desired concentration. That is, it is possible to use a reference liquid of unknown concentration by making the compensation of the dilution ratio according to the present invention. This means that the invention is very conveninet since the reference liquid can be used as it is even when it is questionable as to whether it has an accurate concentration as prescribed or not. Further, a sterilized reference liquid can be used which is adjustable easily by using physiological saltwater, glucose injection, or others. If circumstances require omitting the compensation of the dilution ratio performed by the use of the reference liquid, it is also practicable to make the compensation of the dilution ratio while using the liquid to be tested itself, such as the blood of the patient directly after the catheter is attached to the patient.

We claim:

1. A method for continuously measuring a specified ingredient of a first liquid, said first liquid being diluted with a diluent to form a diluted liquid, while continuously monitoring the concentration of said specified ingredient contained in said first liquid by selecting and mixing said first liquid and said diluent and transferring at least one of said diluted liquid, said diluent and said first liquid by respective tube pumps into a measuring section wherein dilution ratios are determined, said method comprising the steps of:

selecting said diluted liquid at two or more dilution ratios and changing the quantity of at least one of said transferred diluent and said transferred first liquid during said determination in said measuring section to change at least one of said dilution ratios;

determining a real dilution ratio of said diluted liquid at a first period of time, said first period of time occurring when quantities of said transferred liquids have been changed, according to measured values of said specified ingredients determined at said dilution ratios; and determining the concentration of said specified ingredient in said first liquid using said real dilution ratios obtained in any one of periods of time occurring before, after and during said first period of time.

2. The method according to claim 1 further comprising the steps of comparing said real dilution ratio obtained by changing said quantity of transferred liquid having a predetermined dilution ratio $\delta_0$ wherein $\delta_0$ is obtained by using an initial reference liquid at the beginning of the measurement, and further compensating said changed liquid so as to return to the original dilution ratio by adjusting said quantity of one of said transferred first liquid and said transferred diluent.

3. The method according to claims 1 or 2 wherein said first liquid is blood and said diluent is an anticoagulant for diluting said blood, said method further including the step of inserting a double current catheter into a patent, said blood being drawn from said patient and mixed with said anticoagulant via said double current catheter.

4. The method according to claim 3 wherein said double current catheter includes individual catheter tubes for carrying said diluent and said blood each of said tubes being coupled directly to said tube pumps.

* * * * *